United States Patent [19]

Oh et al.

[11] Patent Number: 5,380,818
[45] Date of Patent: Jan. 10, 1995

[54] HIGH MODULUS AROMATIC POLYAMIDE FILM AND PRODUCTION THEREOF

[75] Inventors: Tae-jin Oh, Daegu; Jin-sa Kim, Seoul, both of Rep. of Korea

[73] Assignee: Kolon Industries, Inc., Seoul, Rep. of Korea

[21] Appl. No.: 94,425

[22] Filed: Jul. 16, 1993

[30] Foreign Application Priority Data

Jul. 20, 1992 [KR] Rep. of Korea ............... 92-12920
Jun. 29, 1993 [KR] Rep. of Korea ............... 93-11943

[51] Int. Cl.$^6$ ................ C08G 69/08; C08G 69/26
[52] U.S. Cl. ................ 528/331; 528/310; 528/312; 528/319; 528/335; 528/336; 428/474.4
[58] Field of Search ........... 528/331, 310, 312, 319, 528/335, 336; 428/474.4

[56] References Cited

U.S. PATENT DOCUMENTS

| | | | |
|---|---|---|---|
| 3,622,545 | 11/1971 | Foldi et al. | 528/331 |
| 3,904,519 | 9/1975 | McKinney, Jr. et al. | 210/22 |
| 4,511,709 | 4/1985 | Yoo et al. | 528/312 |
| 5,039,785 | 8/1991 | Irwin | 528/331 |
| 5,093,464 | 3/1992 | Yoon et al. | 528/331 |

FOREIGN PATENT DOCUMENTS 51-81880  7/1976  Japan.
57-17886  4/1982  Japan.

OTHER PUBLICATIONS

Macromolecules, vol. 24(15), Jul. 22, 1991, S. M. Aharoni, "Gels of Two-Step Rigid Polyamide Networks", pp. 4286–4294.
CA 71(10): 39573e "Heat-Stable Polymers VIII Poly (N–arsyl–anthranilamides) and their condensation products", Rabil-Loud et al., Sep. 8, 1969.
CA(90), :186896h, "Synthesis of polyquinazolones by the method of modified reducing polyheterocyclization", Korshak et al., 1979 month of publication of other references is not available and will not be printed on the patent.
Polymer Journal, vol. 1, No. 4, pp. 425–431, 1970, M. Kurihara, et al., "Cyclopolycondensation, XIII. Polymer Reactions of Polybenzoxaziones with Organic Base".

Primary Examiner—John Kight, III
Assistant Examiner—P. Hampton-Hightower
Attorney, Agent, or Firm—Oblon, Spivak, McClelland, Maier & Neustadt

[57] ABSTRACT

A novel aromatic diamino amide monomer of the structural formula (I), a novel aromatic polyamide of the structural formula (II) prepared by polycondensation of the monomer and an aromatic diacid halide, and an aromatic polyamide film produced from the polyamide which has high strength as well as high modulusity.

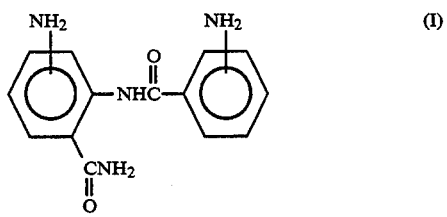

(I)

wherein, each of two $NH_2$ groups may be in meta or para-position to the amide bond.

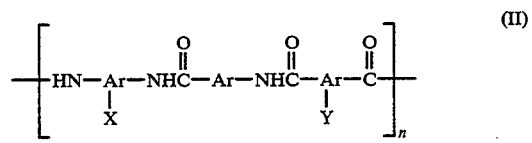

(II)

wherein, Ar represents a phenyl group, X represents $CONH_2$ group in ortho-position to the amide bond, Y represents H, Cl, Br, I, $NO_2$ or an alkyl or alkoxy group having 1 to 4 carbon atom, and n represents an integer between 10 and 100,000.

13 Claims, No Drawings

HIGH MODULUS AROMATIC POLYAMIDE FILM AND PRODUCTION THEREOF

BACKGROUND OF THE INVENTION

(1) Field of the Invention

The present invention relates to an aromatic polyamide film, in particular to a novel aromatic diaminoamide monomer, a high molecular weight aromatic polyamide produced by polymerizing the monomer, having high strength, high modulus, high viscosity and excellent heat-resistance, a high modulus aromatic polyamide film produced from the polymer and processes for production thereof.

(2) Description of the Prior Art

In general, aromatic polyamide films are used valuably in composite materials of air craft and automobile industry, building materials and leisure and sports goods because they have a light weight as well as high strength, high modulus, heat-resistance and abrasion resistance, and in some cases, insulating property.

Due to such utility, there have been developed various processes for producing polyamide film, including Kurihara et al.'s wherein polybenzoxazinone is reacted with ammonia or aniline to open the ring, thereby an aromatic polyamide having two amide substituents is obtained and then it is heat-treated to produce polyquinazolone which is a pure heterocyclic polymer [Polymer Journal Vol. 1, No. 4, pp 425–431 (1970)]. However, the heterocyclic polymer, polyquinazolone is so brittle that the products produced therefrom have poor endurance and abrasion resistance.

Japanese Patent Publication No. Sho. 57-17886 discloses a process wherein polyphenylene terephthalamide is dissolved in sulfuric acid to prepare an optical anisotropic liquid crystalline polymer and then it is discharged, converted to an isotropic polymer by the phase transition technique just before the coagulating bath and made into a film. This process includes the use of sulfuric acid which leads to difficulty in process control and occurrence of environmental contamination.

Japanese Patent laid-Open No. Sho. 51-81880 discloses a film making process wherein a polyphenylene terephthalamide derivative is prepared in order to use an organic solvent instead of sulfuric acid, thereafter the polymer is made into a film, which process has a drawback in that the film obtained has a poor heat-resistance and mechanical strength.

SUMMARY OF THE INVENTION

An object of the present invention is to provide a novel aromatic diaminoamide monomer which can be used to produce a polymer having excellent properties.

Another object of the present invention is to provide a novel aromatic polyamide having high strength, modulus and excellent heat resistance. This novel aromatic polyamide can be dissolved in a polar organic solvent and has an amide group substituted in ortho-position of the aromatic rings, which enables the polymer solution to be spun or made into a film as it is.

The other object of the present invention is to provide an aromatic polyamide film having high strength, modulus and excellent heat resistance and transparency.

In order to achieve the above objects, the present invention provides an aromatic diaminoamide compound represented by the following structural formula (I).

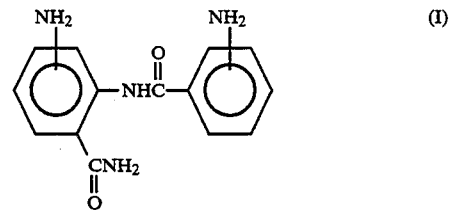

(wherein, each of two $NH_2$ groups may be in meta or para-position to the amide bond.)

The present invention also provides an aromatic polyamide represented by the following structural formula (II).

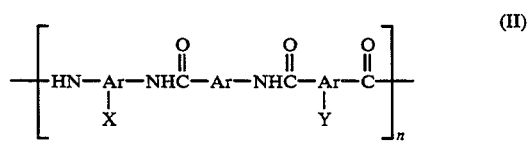

(wherein, Ar represents a phenyl group, X represents $CONH_2$ group in ortho-position to the amide bond, Y represents H, Cl, Br, I, $NO_2$ or an alkyl or alkoxy group having 1 to 4 carbon atom, and n represents an integer between 10 and 100,000.)

In addition, the present invention provides a process for producing an aromatic polyamide polymer represented by the above structural formula (II), which comprises reacting by polycondensation an equimolar amount of an aromatic diaminoamide of the above structural formula (I) and an aromatic diacid halide at 0° to 50° C. temperature for 1 to 50 minutes.

Additionally, the present invention provides a film made from an aromatic polyamide represented by the formula (II), characterized by a tensile modulus of 1,000 $kg/mm^2$ or higher.

Further, the present invention provides a process for producing a polyamide film, comprising the steps of forming a film sheet of a polymer solution of an aromatic polyamide represented by the formula (II); i) fixing to prevent shrinkage, drying and heat-treating the gel film, or ii) drawing the gel film in the non-dried state, and then fixing to prevent shrinkage, drying and heat-treating the film.

DETAILED DESCRIPTION OF THE INVENTION

The novel aromatic diaminoamide monomer represented by the above formula (I) can be produced by the following process.

As shown in the following reaction scheme I, an equimolar amount of 5(or 4)-nitro-2-aminobenzamide (1) and 4(or 3)-nitro benzoylchloride (2) are reacted by condensation using pyridine as a catalyst to obtain 4(or 3), 4'(or 3')-dinitro-6-carbamoyl benzanilide (3) which is then reduced by hydrogen gas using Pd/C catalyst with heating under pressure, finally to obtain 4 (or 3), 4'(or 3')-diamino-6-carbamoyl benzanilide (4).

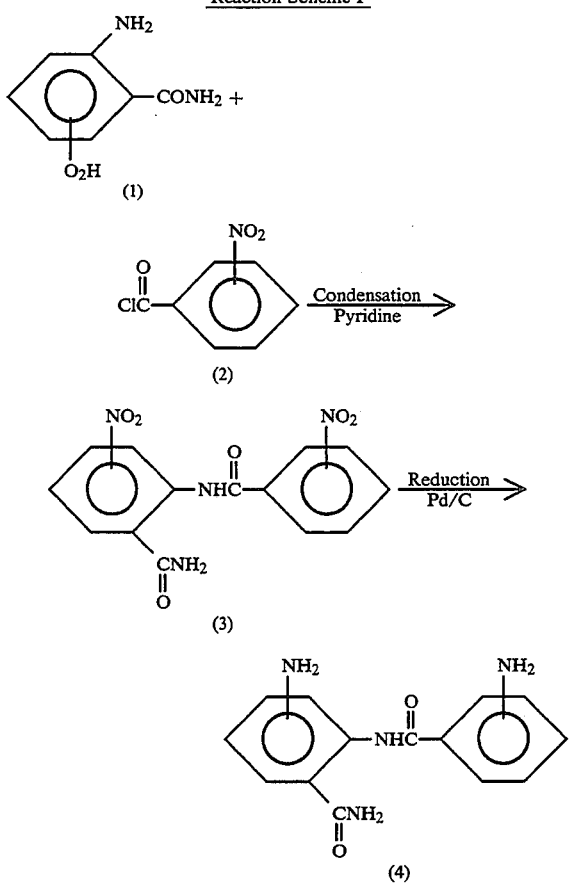

Reaction Scheme I

The process for producing an aromatic polyamide by the polycondensation of an aromatic diaminoamide of the formula (I) and an aromatic diacid halide comprises the following steps:

a) preparing a solvent for polymerization from amide type solvent, urea type solvent, sulfoxide type solvent or a mixture thereof, b) adding and dissolving the aromatic diaminoamide in the solvent for polymerization, c) adding pyridine as a polycondensation catalyst in the obtained solution, d) adding the aromatic diacid halide in the solution with vigorous stirring at 0° to 50° C. temperature, and e) continuing the stirring during 1 to 50 minutes at the temperature to polycondense the monomers, thereby to obtain a high viscous polymer solution.

As the solvent for polymerization, all the organic solvent of amide or urea type can be used but it is desirable to use N-methyl-2-pyrrolidone (NMP), N,N-dimethyl acetamide (DMAc), hexamethyl phosphoramide (HMPA), N,N,N',N'-tetramethyl urea (TMU), N,N-dimethyl formamide (DMF), dimethyl sulfoxide (DMSO) or a mixture thereof.

The solvent for polymerization used in the present invention may be further added with an inorganic salt in order to increase the solubility.

Typical examples of the inorganic salt include alkali metal halide or alkali earth metal halide such as $CaCl_2$, LiCl, NaCl, KCl, LiBr and KBr.

The added amount of the inorganic salt is desirably 12 percent by weight or lower based upon the weight of solvent for polymerization. The amount higher than 12 percent by weight is economically disadvantageous because the desired effects cannot be expected to increase.

Typical examples of the aromatic diacid halide include phthalic dichloride, isophthalic dichloride and terephthalic dichloride which may be unsubstituted or substituted with Cl, Br, I, $NO_2$ or alkyl or alkoxy group having 1 to 4 carbon atom.

The aromatic polyamide represented by the above formula (II) is a novel high molecular weight aromatic polyamide having a limiting viscosity of 3.0 or higher, desirably 2 to 10, which is soluble in a polar organic solvent and has an amide group substituted on the aromatic nucleus.

The limiting viscosity can be calculated from the following formula by the measurement using ubbelohde viscometer and extrapolation of about 5 selected dilute concentration (in 98% sulfuric acid at 30° C.).

$$[\eta] = \lim_{c \to o} \frac{\eta sp}{C}$$

$$\eta sp = \eta r - 1$$

$$\eta r = \frac{t}{to}$$

(t: the time period taken for the solution to pass the viscometer, to: the time period taken for the solvent to pass the viscometer, C: the concentration of the solution)

In a process generally used to produce a film, the polymer solution is spread in a film form on a support, immersed in a coagulating bath, washed with water and dried. In the present invention, after washing with water, the gel film is i) fixed to prevent shrinkage and then dried and heat-treated or ii) drawn in the non-dried state and thereafter fixed to prevent shrinkage, dried and heat-treated, thereby to obtain a polyamide film.

The aromatic polyamide represented by the formula (II) does not undergo a conversion of the polymer's chemical structure when heat-treated at a temperature lower than 200° C., but it is converted to a heterocyclic aromatic polyamide due to formation of quinazolone and/or benzoxazinone nucleus by dehydration and de-ammoniation when heat-treated at a temperature of 200° C. or higher.

The heterocyclic aromatic polyamide film having quinazolone and/or benzoxazinone nucleus exhibits higher strength, modulusity and heat resistance than the heterocyclic polymer in Kurihara et al's.

The gel film made from the polyamide represented by the formula (II) is fixed in two axial directions to prevent shrinkage, dried and heat-treated at 200° to 400° C. temperature to produce a polyamide film having a tensile modulus in one direction of 1,000 kg/mm² or higher. Especially, in case that the gel film is drawn in the wet state and then fixed in two axial directions to prevent shrinkage and heat-treated at 200° to 400° C. temperature, a high modulus aromatic polyamide film is obtained which has a tensile modulus in one direction of 1,500 kg/mm² or higher.

The aromatic polyamide film produced by the present invention shows a strong diffraction at $2\theta = 24°$–26° when irradiated with an X-ray in a direction perpendicular to the film surface. The infrared spectrum of the film heat-treated at 200° C. or higher compared to that of one heat-treated at temperature lower than 200° C. shown the new absorption peaks at 1743cm$^{-1}$ (lactone carbonyl) and 1058cm$^{-1}$ (lactone ether), characteristic of benzoxazinone ring, as well as the new absorption peaks at 1677cm$^{-1}$ (lactone carbonyl), 1347cm$^{-1}$ (lactam C-N stretching) and 1622cm$^{-1}$ (cyclic imine stretching), characteristic of quinazolone ring.

That is, the aromatic polyamide is converted by drying and heat-treating at temperatures of 200° C. or higher, to a heterocyclic aromatic polyamide wherein benzoxazinone and quinazolone rings are introduced in the main chains of aromatic polyamide.

This heterocyclic aromatic polyamide is proved to have more excellent heat resistance because it shows an initial weight decrease at temperatures of 300° C. or higher in a nitrogen atmosphere and exhibits a dynamic modulus at 450° C. which corresponds to 60 to 90 percent of its dynamic modulus at room temperature.

The preferred Examples will be described hereinafter to illustrate the present invention, but not limiting it.

EXAMPLE 1

Preparation of aromatic diaminoamide monomer (4,4'-diamino-6-carbamoyl benzanilide) of the formula (I)

a) Preparation of 4,4'-dinitro-6-carbamoyl benzanilide:

150ml of N-methyl-2-pyrrolidone (NMP) is charged into a 1 liter reactor under nitrogen stream, and 28.1g (0.155mol) of 5-nitro-2-aminobenzamide is added and dissolved. After the solution is cooled to 0°-10° C. in a ice-salt bath, 12.5ml of pyridine is added.

Then, the solution is added with 28.7g (0.155mol) of 4-nitrobenzoyl chloride in a powder form with vigorous stirring.

4-nitrobenzoyl chloride is dissolved at the initial period but precipitated soon to form a paste. The nitrogen purge is stopped and further 50ml of NMP is added to facilitate the stirring and then, the solution is stirred during 4 hours. At the end of the period, the precipitate is washed with water sufficiently to a neutral pH and dried in a vacuum oven at 60° C. to obtain a raw product (46.8g) which is then recrystallized.

b) Preparation of 4,4'-diamino-6-carbamoyl benzanilide:

200ml of dimethylacetamide (DMAc) is charged into a 1 liter reactor and added with 15.6g of 4,4'-diamino-6-carbamoyl benzanilide and 1.56 g of Pd/C (10%), then reduced at 75° to 80° C. under 140 psi hydrogen pressure.

The hydrogen pressure does not drop after 80 minutes' lapse and the reaction solution is left standing overnight. Thereafter, the reaction solution is filtered and DMAc distilled off completely. The remaining reaction material is added with water to form a precipitate.

After washing the precipitate with distilled water, it is cooled to a temperature of 10° C. or lower and added with HCl to pH 1-2, thereby the precipitate is dissolved completely to form a transparent solution. The solution is filtered and added with Na$_2$CO$_3$ to pH 8 to form a precipitate. After the dissolving, filtering and precipitating procedure using HCl and Na$_2$CO$_3$ repeated once more, the precipitate is washed sufficiently with distilled water to a neutral pH and dried to obtain a raw product (11.45 g) which is then recrystallized with ethanol, thereby to obtain a final product. This product is identified to be 4,4'-diamino-6-carbamoyl benzanilide by the elemental analysis and NMR spectroscopy.

Elementary analysis:
Theoretical: C 62.21% H 5.22% N 20.73%
Measured: C 62.30% H 5.24% N 21.05%

EXAMPLE 2

Preparation of aromatic polyamide 450 ml of dimethyl acetamide (DMAc) is charged into a 1 liter reactor, and 7.5 g of LiCl is added and dissolved completely to prepare a solvent for polymerization. In the solvent, 20.25 g of 4,4'-diamino-6-carbamoyl benzanilide is added and completely dissolved. Then, 19 ml of pyridine is added and the solution is added with 15.3 g of terephthaloyl chloride at once with vigorous stirring while maintaining the temperature of the solution at 10° to 15° C.

The viscosity of the polymerization solution is gradually increased immediately after the addition and the solution becomes a high viscous polymer solution after a few minutes. The recovered aromatic polyamide has a limiting viscosity of 6.5 (in 98% sulfuric acid at 30° C.).

EXAMPLE 3

Production of aromatic polyamide film

The polymer solution obtained in Example 2 is spread as a film using a doctor blade on a glass plate and immersed in 40% aqueous DMAc solution at 10° C. during 10 minutes and washed with water. The obtained gel film is fixed in two axial directions to prevent shrinkage, dried in an oven at 100° C. during 30 minutes, and heat-treated in a vacuum oven during 30 minutes to obtain a film of 11 μm thickness. The film is by a tensile strength tester (AUTOGRAPH, manufactured by SHIMAJU Co. in Japan) to have a tensile strength of 30 kg/mm$^2$, a tensile modulus of 1,000 kg/mm$^2$ and an elongation of 12%.

EXAMPLE 4

Production of aromatic polyamide film

The polymer solution obtained in Example 2 is spread as a film using a doctor blade on a glass plate and immersed in 40% aqueous DMAc solution at 10° C. during 10 minutes and washed with water. The obtained gel film is drawn in one axial direction by 1.7 times, washed with water. Then the film is fixed in two axial directions to prevent shrinkage, dried in an oven at 100° C. during 30 minutes, and heat-treated in a vacuum oven during 30 minutes to obtain a film of 7 μm thickness. The film is determined by a tensile strength tester to have a tensile strength of 40 kg/mm$^2$, a tensile modulus of 2,100 kg/mm$^2$ and an elongation of 4%.

EXAMPLE 5

Production of aromatic polyamide film

A film obtained by the same procedure as that of Example 4 is subjected to a further heat treatment in a vacuum oven at 250° C. for 30 minutes to obtain a film of 7 μm thickness. The film is tested by a tensile strength tester determined to have a tensile strength of 50 kg/mm$^2$, a tensile modulus of 2,300 kg/mm$^2$ and an elongation of 4%.

EXAMPLE 6

Production of aromatic polyamide film

A film obtained by the procedure same as that of Example 4 is subjected to a further heat treatment in a vacuum oven at 300° C. for 30 minutes to obtain a film of 7 μm thickness. The film is tested by a tensile strength tester and determined to have a tensile strength of 63 kg/mm² a tensile modulus of 2 800 kg/mm² and an elongation of 5%.

EXAMPLE 7

Production of aromatic polyamide film

A film obtained by the same procedure as that of Example 4 is subjected to a further heat treatment in a vacuum oven at 350° C. for 30 minutes to obtain a film of 7 μm thickness. The film is tested by a tensile strength tester and determined to have a tensile strength of 55 kg/mm² a tensile modulus of 2,500 kg/mm² and an elongation of 5%.

EXAMPLE 8

Preparation of aromatic diaminoamide monomer (3,4'-diamino-6-carbamoyl benzanilide) of the formula (I)

a) Preparation of 3,4'-diamino-6-carbamoyl benzanilide:

150 ml of N-methyl-2-pyrrolidone (NMP) is charged into a 1 liter reactor under nitrogen stream, and 28.1 g (0.155mol) of 5-nitro-2-aminobenzamide is added and dissolved. After the solution is cooled to 0°–10° C. in a ice-salt bath, 12.5 ml of pyridine is added.

Then, the solution is added with 28.7 g (0.155mol) of 3-nitrobenzoyl chloride in a powder form with vigorous stirring.

3-nitrobenzoyl chloride is dissolved at the initial period but precipitated soon to form a paste. The nitrogen purge is stopped and further 50 ml of NMP is added to facilitate the stirring and then, the solution is stirred during 4 hours. At the end of the period, the precipitate is washed with water sufficiently to a neutral pH and dried in a vacuum oven at 60° C. to obtain a raw product (46.8 g) which is then recrystallized.

b) Preparation of 3,4'-diamino-6-carbamoyl benzanilide:

200 ml of dimethylacetamide (DMAc) is charged into a 1 liter reactor and added with 15.6 g of 3,4'-dinitro-6-carbamoyl benzanilide and 1.56 g of Pd/C (10%), then reduced at 75° to 80° C. under 140 psi hydrogen pressure.

The hydrogen pressure does not drop after 80 minutes' lapse and the reaction solution is left standing overnight. Thereafter, the reaction solution is filtered and DMAc is distilled off completely. The remaining reaction material is added with water to form a precipitate.

After washing the precipitate with distilled water, it is cooled to a temperature of 10° C. or lower and added with HCl to pH 1–2, thereby the precipitate is dissolved completely to form a transparent solution. The solution is filtered and added with $Na_2CO_3$ to pH 8 to form a precipitate. After the dissolving, filtering and precipitating procedure using HCl and $Na_2CO_3$ is repeated once more, the precipitate is washed sufficiently with distilled water to a neutral pH and dried to obtain a raw product (11.45 g) which is then recrystallized with ethanol, thereby to obtain a final product. This product is identified to be 3,4'-diamino-6-carbamoyl benzanilide by the elemental analysis and NMR spectroscopy.

Elemental analysis:
Theoretical: C 62.21% H 5.22% N 20.73%
Measured: C 62.30% H 5.24% N 21.05%

EXAMPLE 9

Preparation of aromatic polyamide 450 ml of dimethyl acetamide (DMAc) is charged into a 1 liter reactor, and 7.5 g of LiCl is added and dissolved completely to prepare a solvent for polymerization. In the solvent, 20.25 g of 3,4'-diamino-6-carbamoyl benzanilide is added and completely dissolved. Then, 19 ml of pyridine is added and the solution is added with 15.3 g of terephthaloyl chloride at once with vigorous stirring while maintaining the temperature of the solution at 10° to 15° C.

The viscosity of the polymerization solution is gradually increased immediately after the addition and the solution becomes a high viscous polymer solution after a few minutes. The recovered aromatic polyamide has a limiting viscosity of 6.1 (in 98% sulfuric acid at 30° C.).

EXAMPLE 10

Production of aromatic polyamide film

The polymer solution obtained in Example 9 is spread as a film using a doctor blade on a glass plate and immersed in 40% aqueous DMAc solution at 10° C. during 10 minutes and washed with water. The obtained gel film is fixed in two axial directions to prevent shrinkage, dried in an oven at 100° C. during 30 minutes, and heat-treated in a vacuum oven during 30 minutes to obtain a film of 11 μm thickness. The film is tested by a tensile strength tester and determined to have a tensile strength of 30 kg/mm² a tensile modulus of 1,000 kg/mm² and an elongation of 25%.

EXAMPLE 11

Production of aromatic polyamide film

The polymer solution obtained in Example 9 is spread as a film using a doctor blade on a glass plate and immersed in 40% aqueous DMAc solution during 10 minutes and washed with water. The obtained gel film is drawn in one axial-direction by 1.7 times, washed with water. Then the film is fixed in the two axial directions to prevent shrinkage, dried in an oven at 100° C. during 30 minutes, and heat-treated in a vacuum oven during 30 minutes to obtain a film of 11 μm thickness. The film is determined by a tensile strength tester (AUTOGRAPH, manufactured by SHIMAJU Co. in Japan) to have a tensile strength of 35 kg/mm², a tensile modulus of 1,800 kg/mm² and an elongation of 15%.

EXAMPLE 12

Production of aromatic polyamide film

A film obtained by the same procedure as that of Example 11 is subjected to a further heat treatment in a vacuum oven at 300° C. for 30 minutes to obtain a film of 7 μm thickness. The film is tested by a tensile strength tester and determined to have a tensile strength of 52 kg/mm² a tensile modulus of 2,300 kg/mm² and an elongation of 15%.

From the results of Example 1 to 12, it is evident that the aromatic polyamide films produced from the novel aromatic polyamide according to the present invention have high strength and high modulus.

What is claimed is:

1. An aromatic polyamide represented by structural formula (II):

$$\left[ \mathrm{HN{-}Ar{-}NHC(=O){-}Ar{-}NHC(=O){-}Ar{-}C(=O){-}} \right]_n$$
(with X on the first Ar and Y on the third Ar)     (II)

wherein Ar represents a phenyl group, X represents the group CONH$_2$ in the ortho-position to the amide bond, Y is selected from the group consisting of H, Cl, Br, I, NO$_2$, and an alkyl or alkoxy group having 1 to 4 carbon atoms, and n represents an integer between 10 and 100,000.

2. A process for preparing an aromatic polyamide of structural formula (II):

$$\left[ \mathrm{HN{-}Ar{-}NHC(=O){-}Ar{-}NHC(=O){-}Ar{-}C(=O){-}} \right]_n$$    (II)

wherein Ar represents a phenyl group, X represents the group CONH$_2$ in the ortho-position to the amide bond, Y is selected from the group consisting of H, Cl, Br, I, NO$_2$, and an alkyl or alkoxy group having 1 to 4 carbon atom, and n represents an integer between 10 and 100,000, comprising:

(a) adding a solvent to a reactor;
(b) dissolving in the solvent an aromatic diaminoamide of structural formula (I):

[structure showing two NH$_2$-substituted phenyl groups connected by NHC(=O) bridge with a CNH$_2$(=O) substituent]    (I)

wherein each of the two NH$_2$ groups in formula (I) is in the meta or paraposition to the bridging amide bond, to obtain a reaction solution;
(c) adding pyridine to the reaction solution;
(d) adding an aromatic diacid halide to the reaction solution with stirring; and
(e) continuing the stirring to obtain a viscous polymer solution of the aromatic polyamide.

3. The process according to claim 2, wherein said solvent is selected from amide solvents, urea solvents, sulfoxide solvents, or mixtures thereof.

4. The process according to claim 3, wherein said solvent further comprises an inorganic salt.

5. The process according to claim 4, wherein said inorganic salt is at least one selected from the group consisting of CaCl$_2$, LiCl, NaCl, KCl, LiBr and KBr.

6. The process according to claim 4, wherein the amount of said Inorganic salt is up to 12 percent by weight, based on the solvent.

7. An aromatic polyamide film comprising the aromatic polyamide according to claim 1.

8. The film according to claim 7, wherein said polyamide has a limiting viscosity measured in 98% sulfuric acid at 30° C. of 2 or higher.

9. The film according to claim 8, wherein said polyamide film has a limiting viscosity measured in 98% sulfuric acid at 30° C. of between 2 to 10.

10. The film according to claim 7, wherein the tensile modulus is 1,000 kg/mm$^2$ or higher.

11. The process according to claim 2, wherein step (d) is carried out at a temperature of from 0° to 50° C., and wherein step (e) is carried out for from 1 to 50 minutes.

12. The process according to claim 2, wherein said solvent is selected from the group consisting of N-methyl-2-pyrrolidone, N,N-dimethyl acetamide, hexamethyl phosphoramide, N,N,N',N'-tetramethyl urea, N,N-dimethyl formamide, dimethyl sulfoxide and mixtures thereof.

13. The process according to claim 2, wherein said aromatic diacid halide is selected from the group consisting of phthalic dichloride, isosphthalic dichloride and terephthalic dichloride, all of which may be either unsubstituted or substituted with Cl, Br, I, NO$_2$, or an alkyl or alkoxy group having from 1 to 4 carbon atoms.

* * * * *